United States Patent [19]

Haraguchi

[11] Patent Number: 4,698,160

[45] Date of Patent: Oct. 6, 1987

[54] METHOD AND APPARATUS FOR PREPARING HEMODIALYSIS FLUIDS OF ACCURATELY PORTIONED COMPONENTS

[75] Inventor: Masato Haraguchi, Moriyama, Japan

[73] Assignee: Toray Industries, Inc., Tokyo, Japan

[21] Appl. No.: 680,248

[22] Filed: Dec. 11, 1984

Related U.S. Application Data

[63] Continuation of Ser. No. 335,488, Dec. 30, 1981, abandoned, which is a continuation of Ser. No. 124,351, Feb. 25, 1980, abandoned.

[51] Int. Cl.$^4$ ............................................. B01D 13/00
[52] U.S. Cl. ................................. 210/647; 210/321.71
[58] Field of Search ............... 210/188, 647, 321.3; 222/249, 250; 604/80, 81, 407, 410; 417/395

[56] References Cited

U.S. PATENT DOCUMENTS

| | | | |
|---|---|---|---|
| 1,144,583 | 6/1915 | Brown | 222/249 |
| 3,669,880 | 6/1972 | Marantz et al. | 210/22 |
| 4,054,522 | 10/1977 | Pinkerton | 210/188 |
| 4,119,113 | 10/1978 | Meginniss, III | 137/99 |
| 4,209,391 | 6/1980 | Lipps et al. | 137/99 X |
| 4,386,716 | 6/1983 | Buck | 222/250 X |

FOREIGN PATENT DOCUMENTS

| | | | |
|---|---|---|---|
| 2906300 | 8/1979 | Fed. Rep. of Germany | 222/249 |
| 2346238 | 4/1976 | France | 128/272 |
| 1115231 | 5/1968 | United Kingdom | 222/249 |

OTHER PUBLICATIONS

"Specifications: F4M2 Module", sales brochure of Fluid Motoring, Inc., 1-76.

Primary Examiner—Frank Spear
Attorney, Agent, or Firm—Austin R. Miller

[57] ABSTRACT

Method and apparatus for preparing a mixed fluid of accurately portioned components for hemodialysis comprises the use of a closed receptacle of fixed volume. Two or more components for the fluid are introduced into a chamber in the closed receptacle to fill it and the resultant fluid of the portioned and mixed components is delivered from the chamber. One or more of the components is introduced into the chamber in predetermined amounts, the sum of which is insufficient to fill the whole volume of the chamber, before or during which the other component is introduced into the chamber and the other component is introduced into the chamber in an amount sufficient to fill the remaining volume of the chamber. The method and apparatus are suitable for preparing dialysate solutions for the use in hemodialysis.

36 Claims, 12 Drawing Figures

METHOD AND APPARATUS FOR PREPARING HEMODIALYSIS FLUIDS OF ACCURATELY PORTIONED COMPONENTS

This application is a continuation of application Ser. No. 335,488, filed Dec. 30, 1981 which is a continuation of application Ser. No. 124,351, filed Feb. 25, 1980, both now abandoned.

BACKGROUND OF THE INVENTION

This invention relates to a method and apparatus for preparing hemodialysis fluids of accurately proportioned components. Particularly, the invention involves a method and apparatus suitable for preparing dialysate solutions for use in dialysis, ultrafiltration and the like.

It has increasingly been desired to easily and accurately control the concentration of a solution, in various chemical industries as well as in the preparation of various reagents and, in particular, of dialysate solutions for use in the control of metabolic functions, for example, in an artificial kidney system. In order to prepare such a dialysate solution of a constant concentration, there has hitherto been used a technique in which the amounts of concentrate and dilute fluid components are accurately measured separately by the use of a proportional feed pump and the like, and then, mixed together, as is described, for example, in U.S. Pat. No. 3,804,107. However, in such a technique, it is necessary to accurately measure the respective amounts of the concentrate and dilute fluid components and, thus, the necessary apparatus for the preparation of such a solution is inevitably complicated. Such a technique has further drawbacks in that a solution of an inaccurate concentration may often be produced, particularly when the difference in the amounts of fluid components is large, and when the mixing of the components occurs under a condition such that the components are in contact with a gas, such as air, thereby undersirably incorporating the gas into the resultant fluid.

Further, a patient in need of dialysis by an artificial kidney system must go to a hospital several times every week to receive lengthy hemodialysis treatments, which interferes with this return to a normal life. In order to make home treatment of the patient possible, it is necessary to provide a compact dialysis apparatus which can be operated easily and accurately, and thus, the development of such a compact, useful dialysis apparatus has earnestly been desired.

In U.S. Pat. Nos. 4,037,616 and 4,096,059, there is disclosed a method and apparatus for proportioning and mixing fluids utilizing a double acting piston/cylinder unit. However, in these patents, it is difficult to change the proportions of the components during the continuously repeated operations. Furthermore, in publicly disclosed Japanese Patent Application (Kokai) No. 72379/1977, there is disclosed a closed circuit simultaneous dialysis and ultrafiltration system.

BRIEF SUMMARY OF THE INVENTION

The present invention provides a method for preparing a mixed fluid of accurately proportioned components which comprises introducing two or more fluid components into a closed receptacle which has a fixed volume to fill the closed receptacle, and delivering the resultant fluid of the proportioned and mixed components from the receptacle. One or more of the components are introduced into the receptacle in predetermined amounts, the sum of which is insufficient to fill the whole volume of the receptacle, and the other component is introduced into the receptacle in an amount sufficient to fill the remaining volume of the receptacle. The first mentioned component may be introduced all at one time or in portions, either before or during the addition of the other component.

According to the present invention, there is further provided an apparatus for preparing a mixed fluid of accurately proportioned components which comprises a closed receptacle of a fixed volume having chambers for receiving two or more components for the fluid, at least one means of introducing one or more of the components into the receptacle in a predetermined amount, the sum of which is insufficient to fill the whole volume of the chamber, all at one time or in portions, before or during the time when the other component is introduced into the receptacle. This invention further provides a means for introducing the other component into the receptacle in an amount sufficient to fill the entire remaining volume of the chambe, and provides a means for delivering the resultant fluid comprising the proportioned and mixed components from the receptacle for use in a hemodialysis environment.

The method and apparatus according to the present invention involve several preferred embodiments, and can advantageously be applied to an artificial kidney system for hemodialysis for the purpose of the control of metabolic functions.

DESCRIPTION OF THE PREFERRED EMBODIMENTS

Figure 1A:
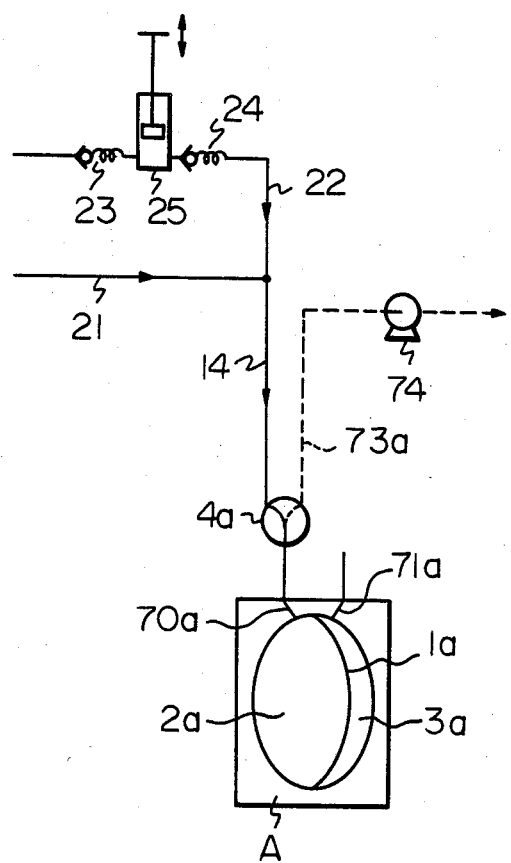
FIG. 1A is a diagrammatic view of an embodiment of the apparatus according to the present invention.

The apparatus illustrated in FIG. 1A comprises a closed receptacle A having an internal chamber having an approximately globular shape and having a constant volume. The receptacle A has two chambers 2a and 3a separated by a partition consisting of a stretchable silicone rubber diaphragm 1a, and the diaphragm 1a can be displaced throughout the whole area of the champ. Fluids are introduced into and delivered from the receptacle through a three-way solenoid valve 4a. The fluid feed line 14 of the receptacle comprises a dilute fluid component feed line 21 and a concentrated fluid component feed line 22. In the concentrated fluid component feed line 22, check valves 23 and 24 and a syringe-type piston pump 25 are provided. A delivery line 73a for delivery of the fluid from the chamber 2a is connected to the three-way solenoid valve 4a and comprises an appropriate pump 74. The chamber 3a has a port 71a which allows displacement of the diaphragm 1a.

When the fluid filled in the chamber 2a has been delivered by the pump 74 and a start signal is applied from a central control system (not shown) when the diaphragm 1a is in close contact with the left side of the inner wall of chamber of receptacle A, the three-way solenoid valve 4a is actuated and the feed of the dilute fluid component through the line 21 is started by driving an appropriate pump (not shown) or by operating a valve (not shown). Subsequently, the piston pump 25 is actuated and the concentrated fluid component, the amount of which has already been measured, is fed into the chamber 2a. The diaphragm 1a, being in close contact with the left side of the chamber of inner wall of the receptacle A, is displaced as the dilute and concentrated fluid components flow into the chamber 2a.

When the diaphragm 1a is finally brought into contact with the right side of the inner wall of the chamber of receptacle A, the feed of the fluid components is stopped by a stop signal from a signal generator (not shown) according to the indication of a pressure gage (not shown). Then, when needed, the resultant fluid, having an accurately controlled concentration is delivered for use through the delivery line 73a by the operation of the pump 74.

After all of the prepared fluid has been delivered for use, the diaphragm 1a is brought into contact with the left side of the inner wall of the receptacle A. At this time, a change in the indication of the pressure gage is communicated to the central control system so that a signal is again transmitted from the central control system to repeat the above-mentioned operation.

In the above-mentioned apparatus, a well, optionally having an agitator, may be provided at an appropriate position in the delivery line for ensuring uniform mixing. Alternatively, the fluid components may be uniformly mixed by shaking the receptacle A. In the case where the prepared fluid is used as a dialysate solution, a heater for regulating the temperature of the solution may be provided at an appropriate position in order to control the temperature relative to the body temperature of the patient. Further, an apparatus for separating gas from the fluid may optionally be provided at a position in the fluid feed line in order to increase the accuracy of the concentration of the resultant fluid.

As is described above with reference to FIG. 1A, the inflow of the fluid components into the chamber 2a is started when the diaphragm 1a is in close contact with the left side of the inner wall of the receptacle A and is continued until the diaphragm 1a is brought into close contact with the right side of the inner wall of the receptacle A. Thus, the total amount of the total fluid components introduced into the chamber 2a is constant. Therefore, by merely feeding a measured amount of the concentrated fluid component from the line 22, it is possible to obtain a fluid of having a constant concentration in every operation without controlling the amount or rate of the feed of the dilute fluid component introduced from the line 21. It is not necessary to employ a positive displacement pump, proportional feed pump or the like for that purpose and, particularly, when a pump of such a type that allows the back flow of fluid, such as a centrifugal pump, is employed, it is not necessary to stop the operation of the pump. Therefore, it is possible to provide an inexpensive and compact apparatus. Since the chamber 2a is a closed system and its contents are not brought into contact with the open air, there is no air inclusion, which allows for accurate control of the concentration of the resultant fluid. Further, the method and apparatus according to the invention are very suitable for preparing a solution which need to be used quickly to avoid trouble, such as precipitation which might take place, if the solution is not used within a short period of time after the preparation thereof.

It is, of course, necessary to start the feed of the dilute and concentrated fluid components in conformity with the start signal from the central control system and to complete the feed of the concentrated fluid component before the diaphragm comes into close contact with the right side of the inner wall of the closed receptacle. According to a feature of the invention, the (measured) feed of the concentrated fluid component should be completed before completion of the (non-measured) feed of the dilute fluid component. Thus, it is possible to complete the feed of the concentrated fluid component before the commencement of the feed of the dilute fluid component or to feed the concentrated fluid component concurrently with the feed of the dilute fluid component. Alternatively, the feed of the concentrated component may be carried out at an appropriate stage during the course of the feeding of the dilute component. The feed of the concentrated fluid component may be carried out all at one a time or in portions If two or more concentrated fluid components must be fed, it is possible to provide a plurality of concentrate fluid feed lines 22. It is also possible to employ a particulate solid instead of the concentrate fluid component.

Figure 1B:
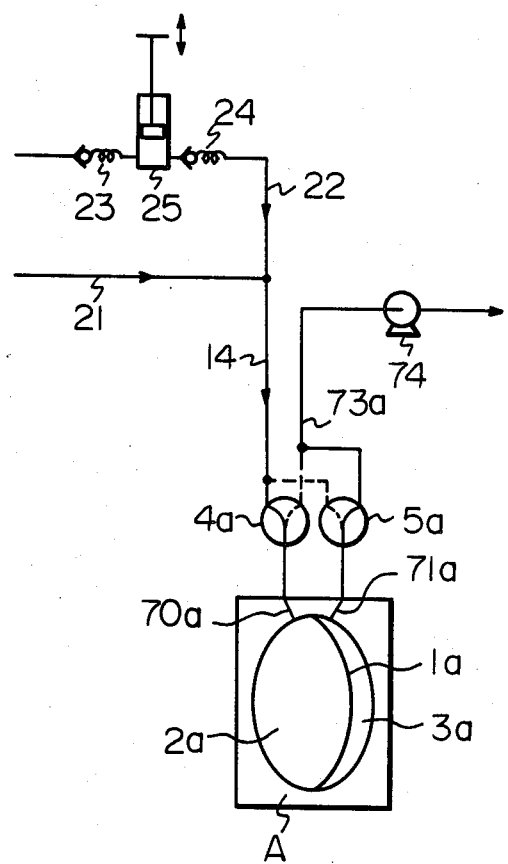
FIG. 1B is a diagrammatic view of another embodiment of the apparatus according to the present invention.

As illustrated in FIG. 1B, the port 71a of the chamber 3a may be connected to the feed line 14 and the delivery line 73a via another three-way electrovalve 5a. In this embodiment, the feed of the fluid components and the subsequent delivery of the resultant fluid can be repeated alternately in the respective chambers 2a and 3a, with every displacement of the diaphragm 1a.

Figure 2A:
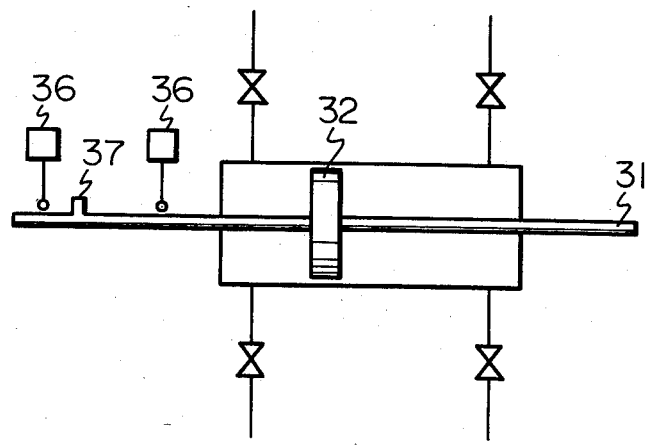
FIG. 2A is a schematic view of a piston and cylinder unit usable as the closed receptacle in the present invention.
Figure 2B:
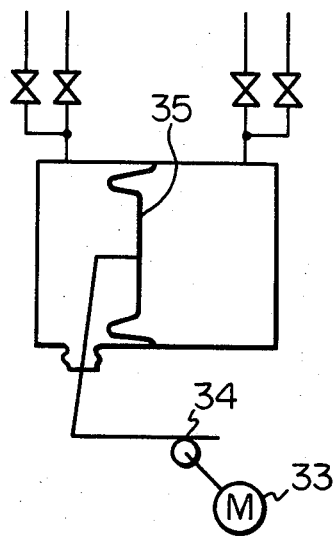
FIG. 2B is a schematic view of a bellows unit usable as the closed receptacle.

The closed fixed volume receptacle employed in the present invention should not be limited to the closed receptacle A having the diaphragm 1a as illustrated in FIG. 1A. Receptacles of the types illustrated in FIGS. 2A and 2B can also be employed, for example. The receptacle illustrated in FIG. 2A is a cylinder/piston unit wherein a head 32 is moved by the reciprocating motion of a piston rod 31. In the receptacle illustrated in FIG. 2B, a bellows 35 is expanded and contracted via a rack and pinion mechanism 34 by the alternate revolutions of a pulse motor 33. In both cases it is necessary to maintain the total amount of the fluid to be introduced into the respective chambers constant and, thus, the stroke of the head 32 is defined by limit switches 36 and a nail 37 in the embodiment as illustrated in FIG. 2A, and the stroke of the bellows 35 is defined by the repetition rate of the pulses applied to the pulse motor 33 in the embodiment as illustrated in FIG. 2B.

Artificial kidneys of various types such as a hollow fiber type coil type and plate type, are known (see, for example U.S. Pat. No. 3,722,695) and, when used for hemodialysis, remove waste components and water from blood by dialysis and ultrafiltration. In such hemodialysis, it is required that the dialysate solution be a prescribed concentration, that the ultrafiltration rate can be accurately controlled and that the dialysis efficiency is high. If the concentration of the dialysate solution is inaccurate, normal metabolism can not be obtained between the dialysate solution and the patient's blood and, in addition, the patient can suffer imbalance syndromes such as headaches or vomiting, or may even face death due to the development of abnormal osmotic pressure in the blood, and of an abnormal balance of water in the cells. If the control of the ultrafiltration rate is inaccurate, the water content in the body fluid may be changed and, thus, the condition of the patient may not improve. Further, low dialysis efficiency may result in unsatisfactory removal of waste components from the blood, or in a lengthy dialysis procedure.

The method and apparatus according to the present invention can advantageously be applied to an artificial kidney system for the purpose of control of metabolic functions. Such an artificial kidney system is compact and inexpensive and makes it possible to automatically prepare a dialysate solution of a prescribed concentration and to measure and control the ultrafiltration rate without lowering the efficiency of dialysis. In particular, according to our extensive study concerning the application of the method and apparatus of the present invention to an artificial kidney system, it has been found that the present invention can be very advantageously applied to the heretobefore-mentioned simultaneous closed circuit dialysis and ultrafiltration system as disclosed in publicly disclosed Japanese Patent Application (Kokai) No. 79732/1977.

Thus, in a system for separating components of a fluid by bringing the fluid to be treated with a dialysate solution through a semi-permeable membrane in a dialysis cell to perform hemodialysis a closed circuit is formed by connecting the dialysate inlet of the dialysis cell to one chamber of a dialysate receptacle which has two chambers separated by a partition, at least a part of which is capable of being displaced, and the dialysate outlet of the dialysis cell to the other chamber of the dialysate receptacle, and the flow of the dialysate solution is generated in the closed circuit by the displacement of said at least a part of the partition, or by other means such as a pump, so that the dialysate solution is fed into and delivered from the dialysis cell. In this system, it is advantageous, in order to make practical hemodialysis possible, to provide two or more dialysate receptacles so that the dialysate solution can be repeatedly prepared.

Figure 3:
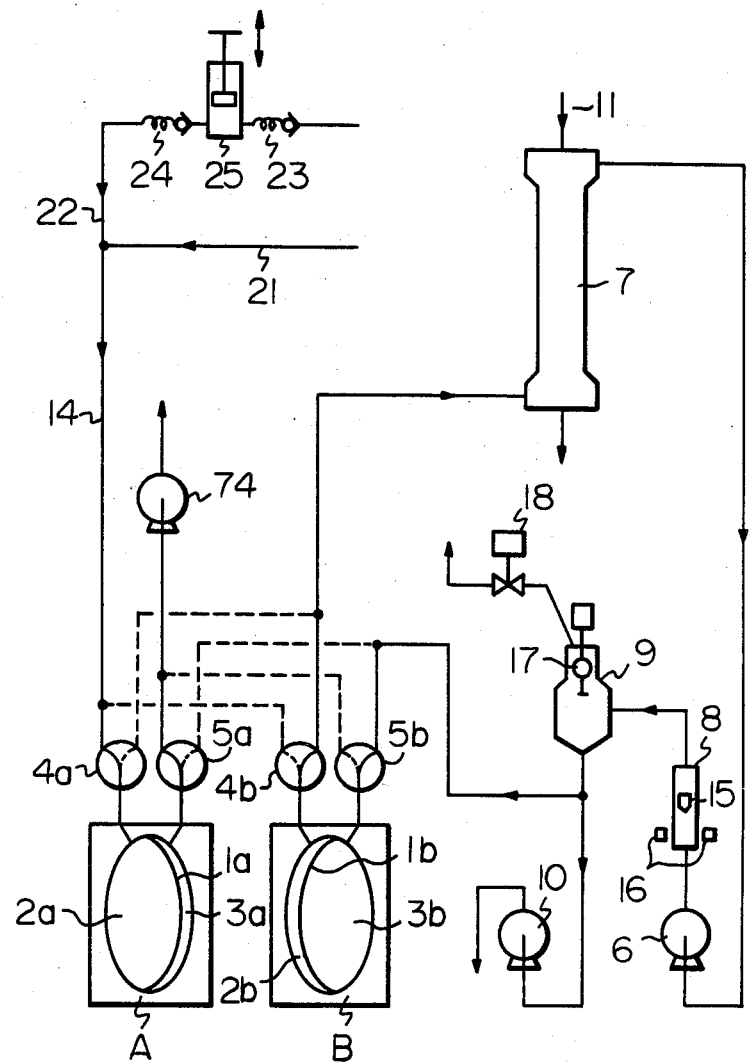
FIG. 3 is a diagrammatic view of a system for separating components of fluid which is advantageously usable as an artificial kidney system and into which an embodiment of the apparatus according to the present invention is incorporated.

An embodiment of such a system is illustrated in FIG. 3, wherein each of the dialysate receptacles A and B has the same construction as that of the receptacle A described above with reference to FIGS. 1A and 1B. The respective receptacles A and B repeat the same operations alternately according to the operation of solenoid valves 4a, 4b, 5a and 5b.

In the condition as illustated in FIG. 3, the receptacle B is connected to a dialysis cell 7. The fresh dialysate solution previously placed in the chamber 2b of the receptacle B is transferred to the dialysis cell 7 and the resulting waste fluid is transferred to the chambr 3b of the receptacle B, in a closed circuit, by a pump 6 via the solenoid valve 4b, the dialysis cell 7, a flowmeter 8, a device 9 for separating gas from fluid, and the electro-valve 5b. Therefore, the amount of the waste fluid transferred from the dialysis cell 7 to the chamber 3b is identical to the amount of fresh dialysate solution transferred from the chamber 2b to the dialysis cell 7, which amount corresponds to the volume of displacement of the diaphragm 1b. If a part of the dialysate solution is removed from the closed circuit by a positive displacement pump 10, water, equal in volume to that of the removed dialysate solution is transferred from the patient's blood (line 11) to the dialysate solution through a semi-permeable membrane in the dialysis cell 7. That is to say, the ultrafiltration rate (i.e. the water-removal rate) can be determined by merely determining the delivery rate of the pump 10.

During the above-mentioned operation, the dialysate receptacle A is isolated from the dialysate receptacle B and the dialysis cell 7 by the solenoid valves 4a and 5a and this part of the system is used to introduce a fresh dialysate solution of accurately proportioned components from line 14 into the chamber 2a, while the waste dialysate solution in the chamber 3a is removed by a pump 74. In the next step the fresh dialysate solution situated in the chamber 2a is used for the dialysis by reversing the positions of the solenoid valves 4a, 4b, 5a and 5b, in a manner as described with reference to FIGS. 1A and 1B.

After the entire amount of the dialysate solution in the chamber 2b has been transferred to the dialysis cell 7, the diaphragm 1b comes into contact with the left side of the inner surface of the receptacle B as illustrated in FIG. 3. Under this condition, since the flow of the solution then stops, a float 15 provided in the flowmeter 8 descends to actuate a pair of photoelectric detectors 16. Thus, a signal from the detectors 16 actuates the solenoid valves 4a, 4b, 5a and 5b to change the connections from the solid lines to the dotted lines, thereby connecting the chamber 2a of the receptacle A filled with the fresh dialysate solution to the dialysis cell 7 while the receptacle B starts to receive another fresh dialysate solution via line 14 and the chamber 2b while the chamber 3b begins to deliver the waste dialysate solution to the waste delivery line. Of course, the waste dialysate solutions may be reused after appropriate refining thereof. It will be appreciated from the above description that the introduction of the dialysate solution into the chamber 2a must be complete before the dialysate solution in the chamber 2b has been completely consumed, and the changeover signal of the electrovalves has been actuated.

The dialysate solution is generally under a negative pressure in the dialysis cell. Thus, if there is any release of gas dissolved in the dialysate solution, or if there is any incorporation of a gas into the dialysate solution due to a leak in the closed circuit, the amount of ultrafiltration is undesirably decreased below the amount of delivery by the pump 10, by an amount corresponding to volume of the gas present in the dialysate solution. A device 9 is used for the removal of such a gas and is provided with a float 17 and a solenoid valve 18. The accumulation of gas present in the dialysate solution is detected by a drop in the level of the float 17, and the gas is removed by release of the solenoid valve 18.

By the above-mentioned system, it has been made possible to accurately control the water-removal rate and to carry out effective dialysis treatment without lowering dialysis efficiency due to impurities in the dialysate solution.

Conventional apparatus for preparing a fluid of a controlled concentration such as a dialysate solution have various drawbacks in that they are expensive, large, inaccurate or unreliable. These drawbacks can effectively be overcome by the present invention. Thus, in the present invention, a fluid of accurately proportions components can easily be prepared by a simple operation by the utilization having a closed receptacle of a fixed volume. That is to say, it is not necessary to feed the dilute fluid component in a controlled amount so long as the receptacle is completely filled with the component. This is a great advantage in the at home treatment of people in need of hemodialysis, since the at home treatment may generally utilize city water as the dilute fluid component and, thus, difficulties may arise such as change of water pressure or interruption of the water supply. Of course, it is not necessary to completely mix the fluid components during the feed of the components, but the components should be appropriately mixed before the resultant fluid is used for the dialysis.

In the present invention, the composition of the resultant fluid can be changed as desired by changing the proportions of the fluid components or by providing two or more feed lines for the concentrated components and changing the feed amounts of the concentrated components through the respective feed lines. In practical hemodialysis, a dialysate solution of a constant concentration which is prepared by diluting a commercial concentrated fluid to an indicated concentration is used uniformly for all patients irrespective of their different conditions. This is because it is troublesome to change the prescription of the dialysate solution for every patient. However, according to the present invention, such inconvenience can easily be overcome.

Further, according to the present invention, there can be obtained a surprising advantage in that the proportions of the fluid components or one or more of the components can be changed as desired even during a dialysis treatment. In general, a patient suffering from chronic renal failure has an osmotic pressure of about 335 mOsm/l due to the accumulation of waste components in the blood, while a man of normal renal function has an osmotic pressure of about 285 mOsm/l. However, the osmotic pressure (X) of usual dialysate solutions is adjusted to a constant value of about 285 mOsm/l in order to adjust the osmotic pressure of the blood to that of a man of normal renal function when the dialysis is completed. For this reason, the following inconvenience may occur.

Figure 4A:
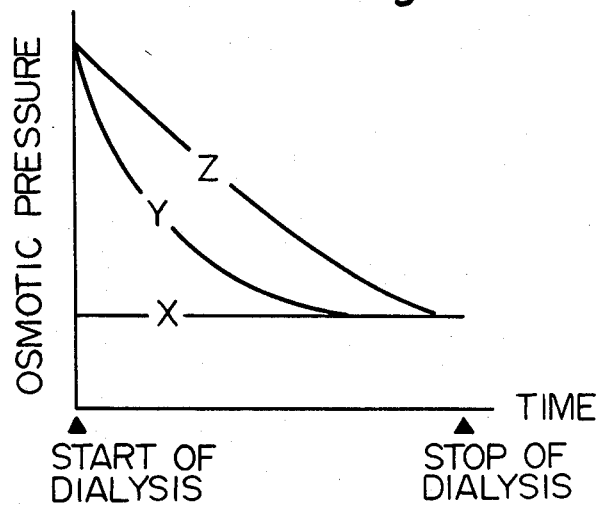
FIGS. 4A and 4B are graphs showing the change of osmotic pressure with duration of dialysis time.

Waste components of low molecular weights including urea, which remarkably increase the osmotic pressure (Y) of the blood of a patient suffering from renal failure, are removed at a relatively early stage in the dialysis. With the removal of the waste components of low molecular weights, the osmotic pressure of the blood is rapidly lowered as illustrated in FIG. 4A. Contrary to this, the osmotic pressure (Z) in the cells is still high at this stage since the transfer of the waste components from the cells to the blood occurs relatively slowly. Therefore, water which is to be naturally transferred from the cells to the blood may be transferred instead from the blood to the cells, which may cause disequilibrium syndrome.

Figure 4B:
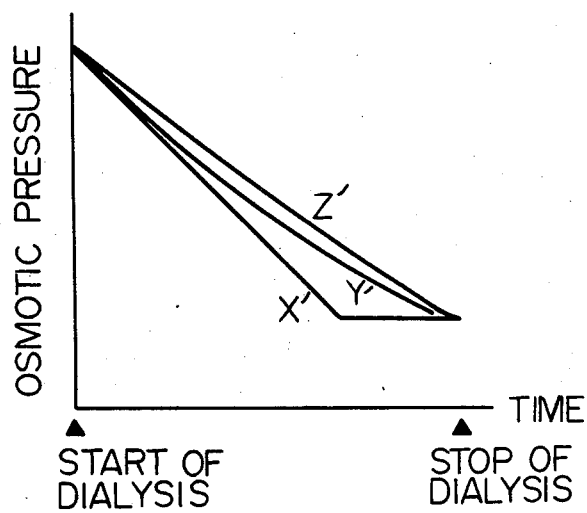

This difficulty may be overcome by setting the osmotic pressure (X') of the dialysate solution, when the dialysis is started, to a level that corresponds to the osmotic pressure (Y') of the blood and gradually lowering the osmotic pressure (X') of the dialysate solution, as illustrated in FIG. 4B. However, this operation is too complicated to use in conventional art.

Figure 5:
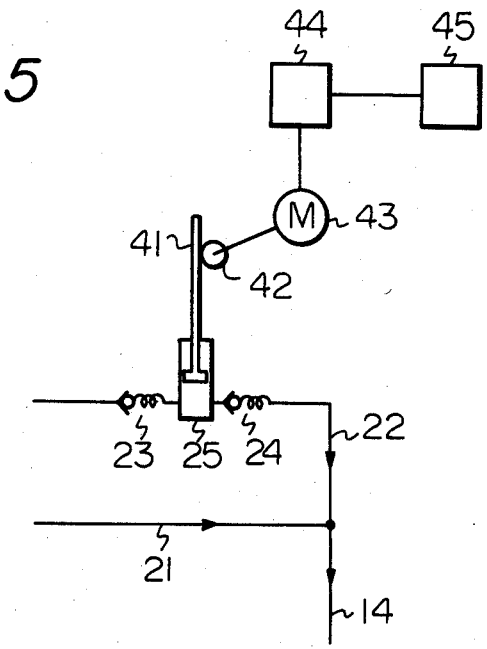
FIG. 5 is a schematic view illustrating an embodiment of the fluid component feed line.

However, according to the present invention, such operation can easily be carried out. Referring to FIG. 5, in the concentrate fluid component feed line 22 as illustrated in FIG. 1A etc., a piston rod 41 of the piston pump 25 is provided with a rack and pinion mechanism 42 which converts the revolutional motion of a pulse motor 43 to the linear motion of the piston rod 41. The pulse motor 43 rotates, alternately in one direction and in the opposite direction, corresponding to the number of pulses applied from a pulse generator 44.

Figure 6:
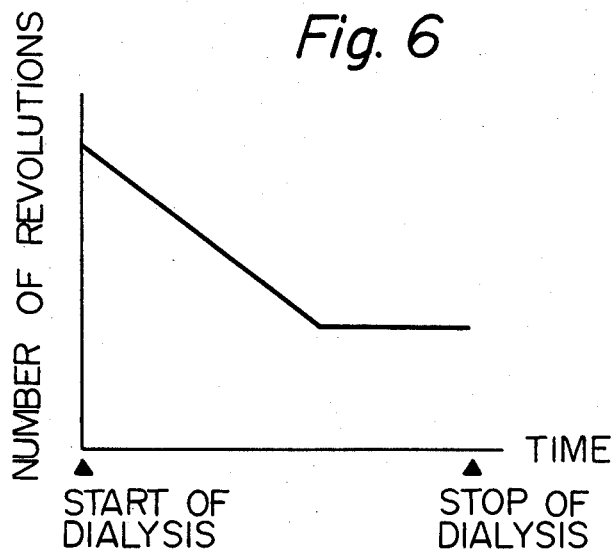
FIG. 6 is a graph showing the change of the number of revolutions to be applied to a motor with duration of 'dialysis time.

When the changeover signal for the receptacles is given, a prescribed number of pulses is applied from the pulse generator 44 to rotate the pulse motor 43 in one direction. Thus, the concentrated fluid component in a measured amount is fed from the piston pump 25 to the feed line 14 through a valve 24 and the line 22. When the pulse reach a prescribed number, i.e. when the feed of a prescribed amount of the concentrated fluid component is completed, the pulse generator applies the same number of pulses as previously applied to the motor 43 to rotate it in the opposite direction, thereby newly feeding the concentrated fluid component into the pump 25 through the valve 23. Again, when the pulses reach a prescribed number, i.e. when a prescribed amount of the concentrated fluid component is fed, the rotation of the motor 43 is stopped and, if necessary, an additional feed into the line 14 is carried out. The number of pulses to be applied to the pulse motor 43 is defined electronically or mechanically by a programmer 45 and is gradually decreased with the progress of the dialysis, as illustrated in FIG. 6. Then, the stroke of the piston rod 41 is decreased and the amount of the concentrated fluid component fed from the pump 25 to line 14 is gradually decreased corresponding to the program. Alternatively, the amount of the concentrated fluid component may be changed by changing the number of strokes of the pump 25.

The dilute fluid component fed from the line 21 is not limited to pure water but may be a solution containing appropriate solute components. For example, in the case where a dialysate solution in which the osmotic pressure is adjusted to 285 mOsm/l is to be fed from the dilute fluid component feed line 21 and a saline solution of a concentration of 10% is to be fed from the concentrated fluid component feed line 22, if the volume of the dialysate receptacle A is 500 ml, the feed amount of the saline solution should be gradually reduced from 7.97 ml when the dialysis is started to 0 ml when the dialysis is stopped, all corresponding to the line $X^1$ in FIG. 4B.

In dialysis treatment, there is a further problem in that a disequilibrium syndrome may occur due to the accumulation or metabolism of acetate which is added to a dialysate solution as a buffer component. In order to avoid this problem, it is desirable to employ bicarbonate instead of acetate. However, as is well known, bicarbonate ions are easily converted to carbonate ions and the carbonate ions an easily bonded to calcium ions present in the dialysate solution which produces precipitates.

This problem can also be overcome advantageously by the present invention. Thus, an increase in the pH value of the dialysate solution may be inhibited as described below with reference to FIG. 3. From the dilute fluid component feed line 21, there is fed a solution containing sodium ions in a concentration of 110 mEq/l and having an osmotic pressure of 237 mOsm/l. This solution contains 3 mEq/l of lactic acid as a pH adjustor and is adjusted to a pH value of about 4.5 so that the pH of the solution is equal to 7.0 to 7.5 after the addition of a bicarbonate solution. To this solution, a solution containing 7% of sodium bicarbonate is added as the bicarbonate solution from the pump 25 to prepare a dialysate solution having a sodium ion concentration of 135 mEq/l, a bicarbonate ion concentration of 29 mEq/l and an osmotic pressure of 286 mOsm/l.

In this way, it becomes possible to carry out the dialysis stably without causing the precipitation of calcium bicarbonate, since the sodium bicarbonate solution is added to the solution having an appropriately adjusted pH just before the feed of the solution into the dialysate receptacle. On the other hand, however, corrosion of the pipe system of the apparatus by lactic acid may occur during prolonged use. This problem can be avoided, as is explained below with reference to FIG. 7. In the embodiment illustrated in FIG. 7, in addition to the concentrate fluid component feed line 22, another concentrate fluid component feed line 51 is provided and this line 51 includes valves 52 and 53 and a piston pump 54. Water is fed from a line 61, and carbon dioxide gas is fed from a bomb 62 and is well dissolved in the water in a mixer 63. Then, the water containing the dissolved carbon dioxide gas is heated by a heater 64 and is subjected to a drop in pressure by a pressure reducing valve 65 to a negative pressure of −600 mmHg. Thus, in this fluid, some gas is contained, such as air liberated from the water and undissolved carbon dioxide gas. This fluid is subjected to pressurization by a pump 67 and the gas is removed by a device 68 for separating gas from fluid. Then, the fluid is fed to the dilute fluid component feed line 21. A concentrate fluid component, the amount of which has been measured by the pump 25 and which does not contain lactic acid, is fed from the line 22, and a sodium bicarbonate solution, the amount of which has been measured by the pump 54 is fed from the line 51. The positions of the lines 22 and 51 may be interchanged.

In this way, the precipitation of carbonate is avoided because of the acidic pH value caused by the dissolved carbon dioxde. It is necessary to provide the heater 64 upstream of the position at which the sodium bicarbonate is added to avoid the precipitation of bicarbonate into the heater surface and carbonization of the glucose. It is preferable, however, that the heater 64 be located upstream of the pump 67 for the efficient removal of the gas. The amount of carbon dioxide gas may be adjusted so that the final partial pressure of carbon dioxide gas is 30 to 60 mmHg.

As explained hereinbefore with reference to FIG. 6, the osmotic pressure of a dialysate solution may be changed as desired by changing amount of the injection of the concentrate fluid. The concentrated fluid to be injected by the pump 25 is not limited to a saline solution but a solution of, for example, glucose, sodium bicarbonate or a mixture thereof. The injection of the concentrated fluid may be effected by using a syringe-type piston pump 25, after a prescribed amount of the concentrate fluid has been measured. Alternatively, the prescribed amount of the concentrated fluid may be injected gradually in portions by means of a constant deivery pump including a so-called metering pump or positive displacement pump such as a diaphragm pump or bellows pump.

The pump 25 and motor 43 illustrated in FIG. 5 are not limited to syringe-type piston pumps and a pulse motor but may include other means which allow the injection of the concentrated fluid in a constant amount. For example, there may be employed a usual positive displacement pump as the pump 25 and an induction motor, DC motor or synchronous motor as the motor 43 and, thus, the pump may be directly connected to the motor. In use of an induction motor or DC motor, the injection of the concentrated fluid may be stopped when the revolutions of the motor reach a prescribed number. On the other hand, in the use of a synchronous motor, the amount of the injection of the concentrated fluid may be controlled by regulating the injection time.

Figure 7:
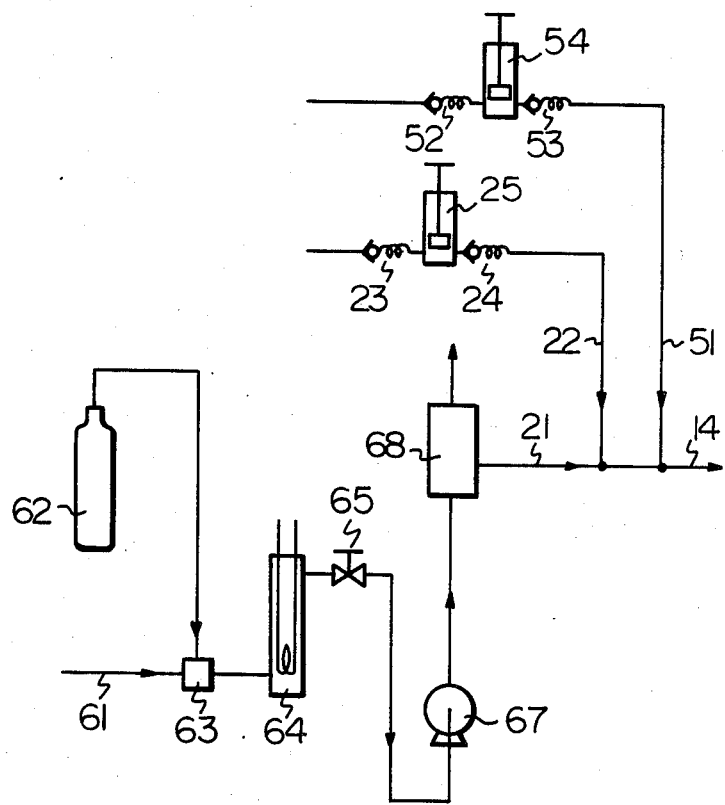
FIG. 7, FIG. 8 and FIG. 9 each illustrates another embodiment of the fluid component feed line.
Figure 8:
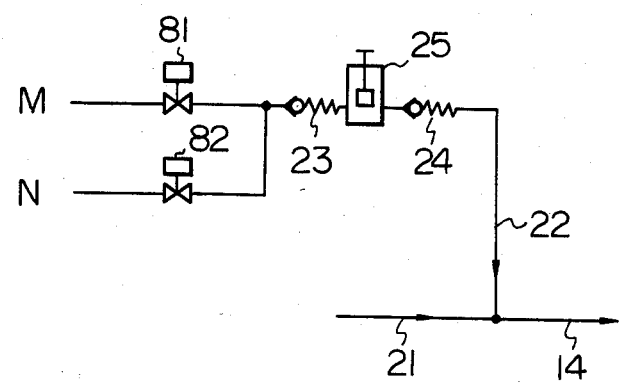

To feed two or more concentrated fluids, it is not always necessary to provide a plurlity of piston pumps as illustrated in FIG. 7. For example, as illustrated in FIG. 8, solenoid valve 81 and 82 may be provided upstream of the check valve 23, and one concentrated fluid M of a prescribed amount may first be fed by opening the valve 81 and closing the valve 82 and next the other concentrated fluid N of a prescribed amount may be fed by opening the valve 82 and closing the valve 81. Thus, the two concentrated fluids may be fed sequentially by one pump.

Figure 9:
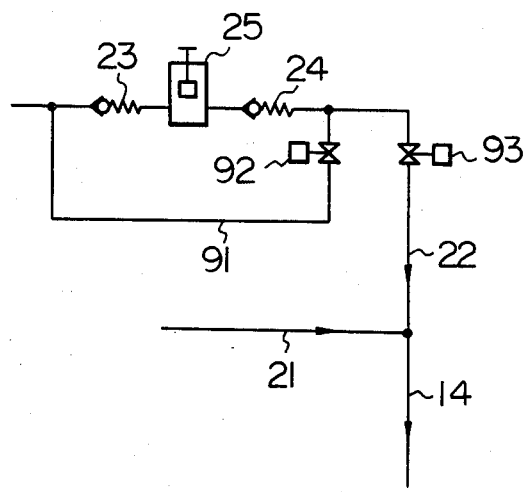

It is not always necessary to stop the pump 25 as illustrated in FIG. 5 after completion of feed of the concentrate fluid in a prescribed amount. For example, as illustrated in FIG. 9, a circuit 91 having a solenoid valve 92 may be provided along with another solenoid valve 93. While the pump 25 is continuously operated, the feed of the concentrated fluid may be carried out by opening the valve 93 and closing the valve 92 and, then, the feed may be stopped by opening the valve 92 and closing the valve 93 to circulate the concentrated fluid in the circuit 91.

The method and apparatus according to the present invention may further be advantageously applied to other artificial organic system such as an artificial liver system.

What is claimed is:

1. In a method for preparing a mixed fluid of accurately portioned components for hemodialysis wherein at least two components are introduced into the chambers of a fixed volume closed receptacle to fill said chambers, and for delivering the resulting fluid, said receptacle having a pair of chambers separated by partition means, at least a part of which partition means is capable of being displaced to change the respective volumes of the chambers such that the amount of volume increase of one chamber is essentially identical to the corresponding volume decrease of another chamber, the steps which comprise:

a. accurately metering an amount of one or more of the fluid components by an independent means and introducing the metered fluid component(s) into one of said chambers of said receptacle, b. introducing an unmetered amount of another of said fluid components into the same chamber of the receptacle to increase the volume of said chamber in an amount sufficient completely to fill said chamber, the unmetered amount being large in relation to the amount of said accurately metered component(s), c. completing step (a) upon or before completion of the step (b), d. closing a feed valve for controlling the feeding or fluid components into the increased volume chamber and then opening a delivery valve for delivering the accurately portioned fluid componenfs from the increased volume chamber in response to the completion of the displacement of the partition means, e. alternately repeating the introduction of the fluid components into each chamber and the subsequent delivery of the accurately portioned fluid components from each said chamber, and f. circulating the accurately portioned fluid components in a closed circuit comprising a dialysis cell and the chambers to perform hemodialysis.

2. A method as claimed in claim 1, wherein said partition is selected from a diaphragm, piston and bellows.

3. A method as claimed in claim 1, wherein said metered component is a concentrated component and said other component is a dilute component.

4. A method as claimed in claim 3, wherein said method is repeatedly carried out and the amounts of said one or more concentrate components are changed as desired.

5. A method as claimed in claim 4, wherein said amounts are gradually decreased.

6. A method as claimed in claim 4, wherein said amounts are intermittently changed.

7. A method as claimed in claim 3, wherein two or more concentrate components are introduced into the receptacle separately through two or more means.

8. A method as claimed in claim 7, wherein gas is incorporated into said dilute component.

9. A method as claimed in claim 1, wherein a pair of said receptacles are provided and said pair of receptacles are operated alternately.

10. A method as claimed in claim 1, wherein a part of the circulating fluid is removed from a location of the closed circuit.

11. A method as claimed in claim 1, wherein gas existing in the circulating fluid is removed from a location of the closed circuit.

12. The method defined in claim 1, wherein the metered component is a single component.

13. The method defined in claim 1, wherein the metered component comprises a plurality of components.

14. The method defined in claim 1, wherein the introduction of all of the metered component is completed before the chamber is filled by completion of introduction of said other component.

15. The method defined in claim 14, wherein the introduction of all of the metered component into said receptacle is completed prior to the introduction of said other component.

16. The method defined in claim 14, wherein the introduction of all of the metered component is introduced along with said other component.

17. The method defined in claim 14, wherein said metered component is introduced into said receptacle chamber as a single portion.

18. The method defined in claim 14, wherein said metered component is introduced into said receptacle chamber as a plurality of portions.

19. The method defined in claim 1, wherein the partition means is a diaphragm.

20. The method defined in claim 1, wherein the partition means is a piston.

21. The method defined in claim 1, wherein the partition means is a bellows.

22. An apparatus for preparing a mixed fluid of accurately portioned fluid components for hemodialysis which comprises:

a. at least two closed fixed-volume multi-chamber receptacles connected for receiving at least two fluid components in the same chamber, said receptacles each having at least two chambers separated by an intervening partition means, at least a part of said partition means being movable to change the respective volumes of said chambers so that one chamber is capable of increasing its volume to reach a predetermined known volume and a volume increase of one chamber is identical to a corresponding volume decrease of the other chamber;

b. a chamber feed means including at least one independent metering means upstream from said chambers for metering in a predetermined amount of one or more measured fluid components into said chambers, said amounts having a volume much less than said predetermined known volume;

c. a further feed means having no metering means connected to said the same chambers for introducing and mixing another fluid component into said chambers in a volume which is sufficient, together with the volume of said one or more metered components, to fill the entire predetermined known volume of said chambers, the amount of unmetered component(s) being large in relation to the amount of said metered component(s);

d. a feed valve for controlling the feeding of fluid components into said chambers, the feed valve being closeable in response to the completion of the displacement of the partition means;

e. a delivery valve for controlling the delivery of the accurately portioned fluid components from the chambers, the delivery valve being openable in response to both (i) the completion of the displacement of the partition means and (ii) the closin of the feed valve; and f. a closed circuit comprising a dialysis cell connected to said receptacles to form a closed circuit in which the accurately portioned fluid components alternately delivered from the receptacles is circulated to perform hemodialysis.

23. An apparatus as claimed in claim 22, wherein each of said two chambers is connected to said feed means and to said delivery line.

24. An apparatus as claimed in claim 22, wherein said partition means is selected from a diaphragm, piston and bellows.

25. An apparatus as claimed in claim 22, wherein said metering means comprises a positive displacement pump capable of measuring the amount of a component and feeding the measured amount of the component.

26. An apparatus as claimed in claim 25, wherein the discharge of said positive displacement pump is changed as desired.

27. An apparatus as claimed in claim 26, wherein said change of the discharge of said positive displacement pump is effected by changing the number of revolutions.

28. An apparatus as claimed in claim 25, wherein said positive displacement pump has two or more inlet lines an the respective connections of said positive displacement pump to said inlet lines are changed by one or more valves.

29. An apparatus as claimed in claim 22, wherein said one or more of the components ae concentrated components and two or more means are provided for separately introducing two or more concentrated components into the receptacle.

30. An apparatus as claimed in claim 22, wherein said other component is a dilute component and a mechanism for incorporating gas into said dilute component is provided in said means for introducing said dilute component.

31. An apparatus as claimed in claim 22, wherein a pir of said receptacles is provided and each of said pair of receptacles is operated alternately.

32. An apparatus as claimed in claim 22, further comprising a means for removing a part of the circulating fluid from a location of the closed circuit.

33. An apparatus as claimed in claim 22, further comprising a means for removing gas existing in the circulating fluid from a location of the closed circuit.

34. The apparatus defined in claim 22, wherein the partition is a diaphragm.

35. The apparatus defined in claim 22, wherein the partition means is a piston.

36. The apparatus defined in claim 22, wherein the partition means is a bellows.

* * * * *